United States Patent
Imagawa et al.

[11] Patent Number: 6,133,324
[45] Date of Patent: Oct. 17, 2000

[54] USE OF PERILLYL ALCOHOL IN ORGAN TRANSPLANTATION

[75] Inventors: David K. Imagawa, Orange; Si Ming-Sing, Santa Ana, both of Calif.

[73] Assignee: The Regents of The University of California, Oakland, Calif.

[21] Appl. No.: 09/305,997

[22] Filed: May 6, 1999

Related U.S. Application Data

[60] Provisional application No. 60/084,644, May 7, 1998.

[51] Int. Cl.$^7$ ...................... A61K 31/045; A61K 31/215; A61K 38/00
[52] U.S. Cl. ............................ 514/729; 514/529; 514/11; 514/19
[58] Field of Search ................................. 514/729, 9, 11, 514/529

[56] References Cited

U.S. PATENT DOCUMENTS 5,470,877  11/1995  Gould et al. ............................. 514/529

FOREIGN PATENT DOCUMENTS

19644422A1  4/1998  Germany.

OTHER PUBLICATIONS

Schultz, S., et al. "Perillic Acid Inhibits Ras/MAPkinase–Driven IL–2 Production in Human T Lymphocytes," pp. 720–725 (1997).

Franklin, R.A., et al. "Ligation of the T Cell Receptor Complex Results in Activation of the Ras/Raf–1/MEK/MAPK Cascade in Human T Lymphocytes," *J. Clin. Invest.*, 93:2134–2140 (1994).

Lazarus, A.H., et al., "Antigen–induced B Lymphocyte Activation Involves the $p21^{ras}$ and ras.GAP Signaling Pathway," *J. Exp. Med.*, 178:1765–1769 (1993).

Hausen, B., et al., "Review of Immunosuppression of Lung Transplantation," *Clinics in Chest Medicine*, v. 18, No. 2, 353–366 (1997).

Woodrow, M., et al., "$P21^{ras}$ and Calcineurin Synergize to Regulate the Nuclear Factor of Activated T cells," *J. Exp. Med.*, 178:1517–1522 (1993).

Phillips, L.R., et al., "Pharmacokinetics of Active Drug Metabolites After Oral Administration of Perillyl Alcohol, an Investigational Antineoplastic Agent, to the Dog," *Drug Metabolism and Disposition*, v.23, No. 7, pp. 676–680 (1995).

First, M.R., "An Update on New Immunosuppressive Drugs Undergoing Preclinical and Clinical Trials: Potential Applications in Organ Transplantation," *Am. J. Kidney Diseases*, vol. 29, No. 2, pp. 303–317 (1997).

*Primary Examiner*—Theodore J. Criares
*Assistant Examiner*—Jennifer Kim
*Attorney, Agent, or Firm*—Oppenheimer Wolff & Donnelly LLP

[57] ABSTRACT

Perillyl alcohol and its monoterpene derivatives used alone or in combination with existing immunosuppressive agents, such as cyclosporine A and azathioprine, to provide methods and compositions which reduce allograft rejection in organ transplant patients.

10 Claims, No Drawings

USE OF PERILLYL ALCOHOL IN ORGAN TRANSPLANTATION

This application claims the benefit of U.S. Provisional Application No. 60/084,644, filed May 7, 1998.

BACKGROUND OF THE INVENTION

1. Field of the Invention

The present invention relates generally to the use of perillyl alcohol and derivatives thereof in organ transplantation. More particularly, the present invention involves the use of perillyl alcohol and/or derivatives thereof alone or in combination with other immunosuppressive agents to reduce allograft rejection in organ transplantation.

2. Description of Related Art

A number of immunosuppressive agents are presently being used to prevent graft rejection. These agents include: cyclosporine A (CsA), tacrilomus (FK506), corticosteroids (e.g. prednisone), mycophenolate mofetil, mizoribine, brequinar sodium, 15-deoxyspergualin, rapamycin, azathioprine, cyclophosphamide, antilymphocyte and antithymocyte antibodies, and muromonab-CD3 (OKT3).

Lymphocytes are the primary immune cells involved in the mammalian immune response. Therefore, inhibiting lymphocyte activation causes significant immunosuppression. Agents such as CsA, FK506 and rapamycin inhibit lymphocyte activation pathways and thus are immunosuppressive agents.

Cytotoxic agents, or agents that kill rapidly dividing cells, can be also used as immunosuppressive agents. One basic lymphocyte function is clonal expansion in order to cause a specific and effective immune response. Therefore, preventing lymphocyte proliferation by use of cytotoxic agents provides another strategy to cause immunosuppression.

There is a present and continuing need to develop novel and effective antirejection agents that have few side effects.

SUMMARY OF INVENTION

The present invention involves the discovery that perillyl alcohol and its oxidative and nucleophilic/electrophilic addition derivatives such as perillic acid, dihydroperillic acid, perillaldehyde and perillic acid methyl ester are effective immunosuppressive agents which may be used to treat organ transplant patients to reduce the possibility of allograft rejection of the transplanted organ. The invention is based on using perillyl alcohol or its derivatives alone or in combination with other immunosuppressive agents to provide methods and compositions which reduce allograft rejection in organ transplant patients.

As a feature of the present invention, existing methods and compositions which utilize relatively toxic immunosuppressive agents to reduce organ rejection in transplant patients are improved by adding perillyl alcohol or perillic acid to the treatment regimen. The relatively low toxicity of perillyl alcohol and its derivatives make them well-suited for replacing or supplementing the commonly used immunosuppressive agents. In addition, monoterpenes including perillyl alcohol and its derivatives have been demonstrated to provide other beneficial effects including anti-cancer, anti-bacterial and anti-fungal properties. These additional properties are especially beneficial to organ transplant patients who have increased risks for certain cancers and opportunistic infections.

The above-described features and attendant advantages of the present invention will become better understood by reference to the following detailed description.

DETAILED DESCRIPTION OF THE INVENTION

In accordance with the present invention, perillyl alcohol and/or its derivatives may be used alone or in combination with one or more other immunosuppressive agents to reduce allograft rejection. For the purposes of this detailed description, the abbreviation "PA" will be used to denote both perillyl alcohol and its derivatives.

Although either perillyl alcohol or its derivatives are effective when used alone, it is preferred that PA be used in combination with other immunosuppressive agents to provide maximum efficacy. Exemplary perillyl alcohol-based immunosuppressive cocktails include: PA/CsA; FK506; PA/CsA; PA/FK506; PA/prednisone; PA/mycophenolate mofetil; PA/mizoribine; PA/brequinar sodium; PA/15-deoxyspergualin; PA/rapamycin; PA/azathioprine; PA/cyclophosphamide; PA/antilymphocyte and antithymocyte antibodies; and PA/OKT3. The relative amounts of PA and other immunosuppressive agent may be varied to establish optimum ratios. In general, it is desirable to minimize the amount of additional immunosuppressive agent in the cocktail while maximizing the PA level. Most immunosuppressive agents have undesirable side effects whereas PA is relatively non-toxic. Accordingly, it is preferred to incorporate additional agents into the PA-based cocktail only to the extent necessary to achieve maximum immune suppression without causing unacceptable side effects.

Perillyl alcohol and PA based cocktails are administered to the transplant patient in the same manner as other immunosuppressive agents. They can be administered orally or intravenously. The particular dosage will vary depending upon whether PA is used alone or as part of an immunosuppressive cocktail. When used alone, dosages of PA on the order of 400 mg/kg/day were found to be effective in preventing acute rejection of heterotopic abdominal heart transplants in rats. This dosage may be reduced. when PA is used as part of one of the above-identified immunosuppressive cocktails. Dosages will also vary depending upon the organ being transplanted and other factors which are routinely taken into consideration during transplant surgery.

Oral administration of PA is preferred. PA alone or in combination with other immunosuppressive agents may be incorporated into any of the well-known pharmaceutical carriers used for oral administration. Examples of suitable carriers or additives for oral administration include soybean oil, olive oil, mineral oil, distilled water, dehydrated alcohol and liposomal microemulsion solutions.

PA is preferably first administered to the patient at least one day prior to the transplant operation. Daily dosing of the patient is continued for at least two to three weeks following the transplant. In accordance with the present invention, PA may induce tolerance in the patient so that continued treatment with PA may not be required in order to prevent organ rejection. The actual post-transplant treatment period will vary from patient to patient and will depend upon the organ being transplanted as well as other factors. Preferably, treatment with PA will continue for about one month after transplantation with the daily doses of PA being gradually reduced thereafter. The patient is carefully monitored and any evidence of organ rejection is treated with a return to full PA dosage. The potential ability of PA to create tolerance in patients is a major advantage over other immune suppression therapies which require long term medication.

Examples of practice and a further description of the invention are as follows:

Perillyl alcohol is a naturally occurring monoterpene with promising chemopreventive and chemotherapeutic properties. Numerous preclinical animal studies have demonstrated its chemopreventive and chemotherapeutic activity, which may be due to its metabolites perillic and dihydroperillic acids. These metabolites (and perillyl alcohol itself) either inhibit protein:prenyl transferases or selectively decrease ras levels by some unknown mechanism. Protein:prenyl transferases transfer the farnesyl and geranylgeranyl moieties from farnesyl- and geranylgeranyl pyrophosphate to small guanine nucleotide binding proteins (G proteins), enabling them to insert into lipid membranes. Despite the unanswered question of how they work, the final effect of PA is selective inhibition of isoprenylation of small (21–26 kDa) G proteins. These proteins include ras superfamily of G proteins (e.g. ras, rho, rab and rap) and several cyclins.

Of particular interest is the inhibition of Ras and related proteins by perillyl alcohol and its metabolites. It has been shown that Ras plays an important role in T and B lymphocyte activation and function. Furthermore, Ras is involved in the positive selection of T lymphocytes in the thymus. Woodrow et al. (p21 ras and calcineurin synergize to regulate the nuclear factor of activated T cells, *Journal of Experimental Medicine* 178, 1517–1522 (1993)) found that Ras synergizes with calcineurin in T lymphocyte activation and independently suggested that inhibiting Ras may be a method of causing immunosuppression. The other small G proteins inhibited by PA are also involved in key lymphocyte functions such as activation, motility, oxidative burst production and proliferation.

It has been shown previously that pravastatin, an HMG-CoA reductase inhibitor (the rate limiting enzyme in the cholesterol synthesis pathway) and weak Ras small G protein inhibitor, in conjunction with cyclosporine reduces the incidence of chronic rejection in cardiac and renal transplant patients and animal transplant models. We have also shown that pravastatin abrogates natural killer cell cytotoxicity and peripheral blood mononuclear cell proliferation, and that this inhibition is mediated by farnesyl pyrophosphate depletion. Farnesyl pyrophosphate is a metabolite of the cholesterol synthesis pathway and thus it can be appreciated that pravastatin causes an effective depletion of farnesyl pyrophosphate, and perillyl alcohol and perillic acid cause a functional depletion of farnesyl pyrophosphate. Hence, farnesyl pyrophosphate depletion, whether it be effective or functional, causes inhibition of the Ras superfamily of proteins.

The following examples demonstrate that perillyl alcohol, a purported Ras inhibitor and chemopreventive and chemotherapeutic agent, prevents graft rejection in a rat heart transplant model. We also demonstrate the immunosuppressive effects of perillyl alcohol and its major metabolite perillic acid on T lymphocytes in vitro.

Animal Model

Hearts from rats of Wistar strain were heterotopically transplanted into the abdomen of rats of Lewis strain. Briefly, Wistar rats (250–300 gm) were anesthetized and their hearts and thoracic aortas removed. The vena cavae of the grafts were ligated. These grafts were then transplanted into the abdomen of Lewis rats (250–300 gm) by anastamosing the graft aorta to the abdominal aorta of the host and the graft pulmonary artery to the host inferior vena cava.

Lewis recipients were fed 400 mg/kg dose of perillyl alcohol intragastrically (ig) on the night before transplant. Thereafter, the recipients received a 400/mg/kg/day dose up to day 30. Control recipients did not receive perillyl alcohol treatment. Graft function was assessed daily by palpation of the graft. Failure to feel the cardiac graft beating warranted an exploratory laparotomy to confirm acute graft rejection. Treated rats gained weight over the treatment period and displayed normal activity.

A total of 24 rats were transplanted. There were 12 untreated rats of which several were sacrificed on days 4 and 6 for histopathological studies, and the rest were allowed to live in order to assess graft survival. Untreated recipients rejected their hearts consistently by day 8, whereas animals treated with 30 days of perillyl alcohol maintained excellent graft function even after cessation of treatment ($p<0.001$, logrank test). Sixty-three percent of the treated animals had grafts which functioned indefinitely.

Histopathology

Histological studies of cardiac allografts from control animals sacrificed on days 4 and 6 showed severe cellular rejection. Day 4 control grafts showed moderate diffuse lymphocytic infiltrate and patches of inflammation. Day 6 control grafts showed large areas of intense inflammation, myocyte necrosis and vasculitis. Grafts from treatment animals obtained at day 6 showed intense inflammation but without evidence of myocyte necrosis. Interestingly, allografts from perillyl alcohol treated animals sacrificed on day 75 showed no inflammation, mild myocyte edema and no vasculitis. No histological differences were found between the grafts and the native thoracic heart or syngeneic transplants.

PHA Induced Peripheral Blood Mononuclear Cell and T Lymphocyte Proliferation are Inhibited by Perillyl Alcohol and Perillic Acid A fundamental measure of immune function is immune cell proliferation. Here we describe that PHA induced peripheral blood mononuclear cells and T lymphocyte proliferation are inhibited by both perillyl alcohol and one of its major metabolites perillic acid. Peripheral blood mononuclear cells were obtained from normal subjects. Briefly, venous blood from healthy subjects were collected in tubes with acid citrate dextrans preservative. The blood was centrifuged and the buffy white coat aspirated and subsequently resuspended in RPMI media. The cell solution was then layered on Ficoll, centrifuged and washed 3 times. T lymphocytes were isolated by incubating peripheral blood mononuclear cells with T-Lymphokwik, a cocktail of antibodies against all cellular components of human blood except T lymphocytes. The serum from the blood was saved for supplementation of RPMI media later in the experiment. Peripheral blood mononuclear cells and T lymphocytes were dispensed into a 96 well microtiter plate with RPMI and 10% autologous serum. Perillyl alcohol and perillic acid stock solutions were prepared by mixing perillyl alcohol with RPMI. Before adding perillyl alcohol solution and perillic acid to the wells, the mixtures were vortexed well. All treatments were performed triplicate or quadruplets. PHA was used to stimulate the peripheral blood mononuclear cells to proliferate for 72 hours. The amount of proliferation was quantified with the MTT assay.

Perillyl alcohol and perillic acid inhibit peripheral blood mononuclear cell and T lymphocyte proliferation in a dose dependent fashion.

The above examples show that perillyl alcohol is able to prevent acute graft rejection in a rat heart transplant model. As an antirejection agent, perillyl alcohol has many attractive qualities. First, it most likely works in a pathway independent of cyclosporine and tacrilomus and thus may be used in conjunction with these established anti rejection drugs. Combination with perillyl alcohol may allow lower dosing of cyclosporine and tacrilomus and thus less side effects. Furthermore, we have shown that perillyl alcohol alone is sufficient to inhibit acute graft rejection, and monotherapy with this drug is certainly feasible. The current human experience of pharmacological doses of perillyl alcohol has been limited to several National Cancer Institute sponsored Phase I and II clinical trials of this agent as a chemopreventive and chemotherapeutic agent. Ripple et al. (Phase I Clinical Trial of Perillyl Alcohol Administered Daily, *Clinical Cancer Research* 4, 1159–1164 (1998)) have reported that the main toxicity of perillyl alcohol administered to their patients was gastrointestinal and included nausea and vomiting, anorexia and eructation.

The other effects of perillyl alcohol will prove to be very beneficial in transplant patients. Transplant patients have a higher risk of developing certain cancers including lymphomas and squamous cell carcinomas. Perillyl alcohol is currently being investigated as a potential chemotherapeutic/chemopreventive agent by the National Cancer Institute. Perillyl alcohol shows antitumor properties in various animal models at doses that were used in our examples to prevent graft rejection. Transplant patients also have an increased risk of developing opportunistic infections from bacterial and fungal microbes. Perillyl alcohol has been shown to be antibacterial as well as antifungal in vitro. Thus many of the potential "side effects" of perillyl alcohol in the transplant patient are actually very beneficial in combating some of the serious complications of organ transplantation.

Our experiments with perillyl alcohol also indicate that p21 Ras inhibitors as a class of drugs may prove to be effective antirejection as well as in autoimmune diseases such as systemic lupus erythematosus, rheumatoid arthritis, and scleroderma.

Heart transplants set forth in the above examples were performed in a highly disparate rat strain combination. When these animals received no immunosuppression, the hearts rejected by day 8. We fed these animals perillyl alcohol (400 mg/kg/day) for a total of 30 days following transplants. Medication was then discontinued. Nevertheless the hearts continued to beat and the animals were ultimately sacrificed at postoperative day 70. Final pathology and analysis of these grafts showed absolutely no evidence of rejection. This result suggests that perillyl alcohol may induce tolerance.

Having thus described exemplary embodiments of the present invention, it should be noted by those skilled in the art that the within disclosures sures are exemplary only and that various other alternatives, adaptations and modifications may be made within the scope of the present invention. Accordingly, the present invention is not limited to the above preferred embodiments, but is only limited by the following claims.

What is claimed is:

1. A method for treating a transplant patient wherein said patient receives a donor organ and wherein there is a possibility of allograft rejection of said organ, said method comprising the step of administering to said patient an immunosuppressive effective amount of perillyl alcohol or a derivative thereof, said step of administering said perillyl alcohol or derivative thereof being carried out for a sufficient time to create tolerance in said patient to said allograft rejection of said organ.

2. A method for treating a transplant patient according to claim 1 wherein said perillyl alcohol or a derivative thereof is administered to said patient both before and after said patient receives said donor organ.

3. A method for treating a transplant patient according to claim 1 wherein said perillyl alcohol or a derivative thereof is administered to said patient orally.

4. A method for treating a transplant patient according to claim 1 wherein an immunosuppressive agent is also administered to said transplant patient, said immunosuppressive agent being selected from the group consisting of cyclosporine A, tacrilomus, corticosteriods, mycophenolate mofetil, mizoribine, brequinar sodium, 15-deoxyspergualin, rapamycin, azathioprine cyclophosphamide, antilymphocyte antibodies, antithymocyte antibodies and muromonab-CD3.

5. A method for treating a transplant patient according to claim 4 wherein said immunosuppressive agent is cyclosporine A.

6. In a method for treating an organ transplant patient wherein a given dosage of immunosuppressive agent is administered to said patient to reduce the possibility of allograft rejection, the improvement comprising the step of reducing the amount of said given dosage of said immunosuppressive agent and administering to said patient an immunosuppressive effective amount of perillyl alcohol or a derivative thereof, said step of administering said perillyl alcohol or derivative thereof being carried out for a sufficient time to create tolerance in said patient to said allograft rejection of said organ.

7. An improved method according to claim 6 wherein said immunosuppressive agent is selected from the group consisting of cyclosporine A, tacrilomus, corticosteriods, mycophenolate mofetil, mizoribine, brequinar sodium, 15-deoxyspergualin, rapamycin, azathioprine cyclophosphamide, antilymphocyte antibodies, antithymocyte antibodies and muromonab-CD3.

8. An improved method according to claim 7 wherein said immunosuppressive agent is cyclosporine A.

9. An improved method according to claim 5 wherein said perillyl alcohol or a derivative thereof is administered to said patient orally.

10. An improved method according to claim 5 wherein said perillyl alcohol or a derivative thereof is administered to said patient both before and after transplantation of said organ.

* * * * *